United States Patent
Rivard et al.

(10) Patent No.: US 8,383,187 B2
(45) Date of Patent: Feb. 26, 2013

(54) ROUGH POROUS CONSTRUCTS

(75) Inventors: Kori Rivard, Warsaw, IN (US); Jeff Rybolt, Fort Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 532 days.

(21) Appl. No.: 12/688,023

(22) Filed: Jan. 15, 2010

(65) Prior Publication Data

US 2010/0209666 A1    Aug. 19, 2010

Related U.S. Application Data

(60) Provisional application No. 61/153,843, filed on Feb. 19, 2009.

(51) Int. Cl.
*A61F 2/02* (2006.01)
*A61F 2/28* (2006.01)
*A61L 27/30* (2006.01)
*B05D 3/00* (2006.01)

(52) U.S. Cl. .................. 427/2.26; 428/148; 623/16.11; 623/23.5

(58) Field of Classification Search ................ 427/2.26; 428/148; 623/16.11, 23.5
See application file for complete search history.

(56) References Cited

U.S. PATENT DOCUMENTS

2008/0300682 A1 * 12/2008 Rivard et al. ............... 623/11.11
2012/0022662 A1 *  1/2012 Conway et al. ............. 623/22.21

* cited by examiner

*Primary Examiner* — Timothy Vanoy

(57) ABSTRACT

The present invention provides a method for processing a green body comprising a powder mixture in which a metal powder and a space filler assume respective positions, comprising applying a material that comprises aspherical metallic particles to at least one surface of the green body, thereby forming a coating on the green body. The present invention also provides implants that are produced in accordance with such method.

17 Claims, 1 Drawing Sheet

ROUGH POROUS CONSTRUCTS

CROSS REFERENCE TO RELATED APPLICATIONS

The present invention claims priority to U.S. Provisional App. No. 61/153,843, filed Feb. 19, 2009, which is hereby incorporated by reference in its entirety.

TECHNICAL FIELD

The present invention pertains to, among other things, coatings for metal substrates, such as those used to prepare medical implants.

BACKGROUND

Surface roughness is an important attribute of orthopedic implants that are intended for cementless fixation to bone. High surface roughness can correspond to elevated friction against bone and general stability upon initial implantation, both of which are conducive to long-term stability via bone and tissue ingrowth. Physical or chemical etching techniques are effective for endowing porous constructs with textured surface profiles, but a need exists for additional methods for imparting surface roughness.

SUMMARY

One aspect of the present invention provides methods comprising applying a material that comprises aspherical metallic particles onto at least one surface of a porous construct, thereby forming a coating on the construct. The present disclosure also provides implants that are produced in accordance with the disclosed methods.

In other aspects, there are provided methods for processing a green body comprising a powder mixture in which a metal powder and a space filler assume respective positions, comprising applying a material that comprises aspherical metallic particles to at least one surface of the green body, thereby forming a coating on the green body. Such methods may further comprise sintering the green body, thereby forming an implant. The present invention also provides implants that are produced in accordance with such methods.

DETAILED DESCRIPTION OF ILLUSTRATIVE EMBODIMENTS

Figure 1:
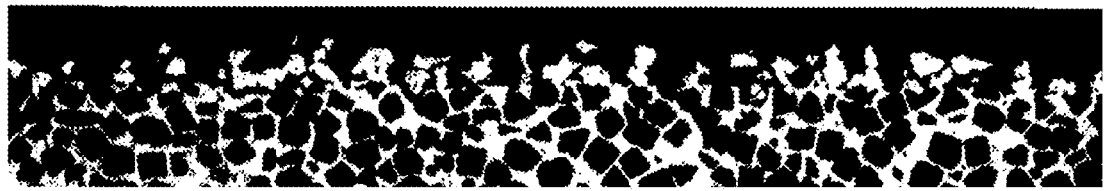
FIG. 1 shows a lateral profile of an irregular porous coating as applied onto a porous substrate in accordance with the present invention.

The present invention may be understood more readily by reference to the following detailed description taken in connection with the accompanying figures and examples, which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

In the present disclosure the singular forms "a," "an," and "the" include the plural reference, and reference to a particular numerical value includes at least that particular value, unless the context clearly indicates otherwise. Thus, for example, a reference to "an adhesive" is a reference to one or more of such adhesives and equivalents thereof known to those skilled in the art, and so forth. When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" refers to a value of 7.2 to 8.8, inclusive; as another example, the phrase " about 8%" refers to a value of 7.2% to 8.8%, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like. In addition, when a list of alternatives is positively provided, such listing can be interpreted to mean that any of the alternatives may be excluded, e.g., by a negative limitation in the claims. For example, when a range of "1 to 5" is recited, the recited range may be construed as including situations whereby any of 1, 2, 3, 4, or 5 are negatively excluded; thus, a recitation of "1 to 5" may be construed as "1 and 3-5, but not 2", or simply "wherein 2 is not included." It is intended that any component, element, attribute, or step that is positively recited herein may be explicitly excluded in the claims, whether such components, elements, attributes, or steps are listed as alternatives or whether they are recited in isolation.

Unless otherwise specified, any of the characteristics, elements, attributes, or steps that are disclosed with respect to one embodiment of the present application may be applied to any other embodiment of the present application.

The disclosures of each patent, patent application, and publication cited or described in this document are hereby incorporated herein by reference, in their entirety.

Metallic porous bodies are well known for use as orthopedic implants and prostheses. The "space holder" method is a widely used process for making metallic foam structures and employs dissolvable or otherwise removable space-holding materials that are combined with metallic powders, compacted, and subsequently removed from the combination by various methods, including heat or liquid dissolution, leaving behind a porous matrix formed from the metallic powder. The porous matrix material is then sintered to further strengthen the matrix structure. Numerous variations on the space holder concept are known in the art. See, e.g., U.S. Pat. Nos. 3,852,045; 6,849,230; U.S. Pub. Nos. 2005/0249625; 2006/0002810. Trabecular metal scaffolds are constructed by applying titanium, tantalum, or niobium to a carbon or polymer foam scaffold by vapor deposition. The structures may further be enhanced by applying and sintering powdered metal (titanium, tantalum, or niobium as appropriate) to the struts of the entire structure to build thickness and strength. These structures are intended to mimic cancellous bone, and provide the high surface area and interconnected, open cell structure that are preferred for encouraging tissue and bone resorption. See U.S. Pat. No. 5,282,861.

Several coating products have been developed for use in connection with solid prosthetic devices, including implant coatings that are said to increase shear strength with bone cement. See, e.g., U.S. Pat. Nos. 5,368,881, 5,658,333. However, these coatings result in a substantially non-porous surface (see U.S. Pat. No. 5,568,333 at col. 4, lines 63-65), which prevents tissue and bone ingrowth and thereby imposes limitations on biological fixation.

Other coatings, such as the POROCOAT® product produced by DePuy Inc. (Warsaw, Inc.) are porous and are intended to maximize tissue ingrowth. POROCOAT® is a three-dimensional, beaded coating that is typically applied to a surface of an orthopedic implant, such as an artificial joint, that is intended to interact with the surface of an adjoining bony surface. Such coatings are applied to the face of an implant in order to impart a rough, high friction surface that interacts with bone in a manner that leads to a decrease in relative movement between the implant and the bone while providing a network of interconnected pores for secure fixation of the implant to bone by the ingrowth of bone tissue.

The present invention pertains to, among other things, methods for providing porous coatings for porous substrates, including porous orthopedic implants. Also provided are implants comprising porous coatings that are applied in accordance with the instant methods. The presently disclosed porous coating products may be applied to one or more of the outer surfaces of bodies for use as orthopedic implants to increase friction between such implants and bone while providing a network of interconnected pores for secure fixation of the implant to bone by the ingrowth of bone tissue. Rough surface coatings exhibit peaks that, when present on an implant face, are believed to lead to increased contact pressure and thereby ploughing and abrasive interaction between the implant face and the surface of an adjoining bone. Such phenomena at the surface of the implant increase the resistance to relative movement between the implant and bone, which corresponds to higher stability upon implantation and may increase the likelihood of achieving biological fixation of the implant.

In one aspect, there are provided methods comprising the step of applying a material that comprises aspherical metallic particles onto at least one surface of a porous construct, thereby forming a coating on the construct. The present disclosure also provides implants that are produced in accordance with the disclosed methods. The term "porous construct" refers to any object, preferably a metallic object, that is characterized by the attribute of porosity with respect to at least a portion of the volume of the object. Preferably, the porous construct has a porosity of about 1% to about 95%, and more preferably about 50% to about 95%, measured with respect to the entire volume of the construct (i.e., including any portions that are not characterized by the attribute of porosity). Porous constructs include objects that are themselves characterized by the attribute of porosity with respect to at least a portion of the volume of the object, but that are attached, adhered, or bound to one or more other objects that are themselves not characterized by the attribute of porosity. The porous construct may be attached, adhered, or bound to one or more non-porous objects prior to or after the material that comprises aspherical metallic particles is applied onto at least one surface of the porous construct.

The porous construct may be a body that has been prepared in accordance with the "space holder" method, described above, such that the porous construct comprises compacted metal powder. The porous construct may be a porous green body (i.e., a porous body that has not been sintered), or may be a sintered body.

The metal powder, and by extension the porous construct, may comprise any biocompatible metal, nonlimiting examples of which include titanium, a titanium alloy (e.g., Ti-6Al-4V), a cobalt-chromium alloy, aluminum, molybdenum, tantalum, magnesium, niobium, zirconium, stainless steel, nickel, tungsten, or any combination thereof. In accordance with known methods for forming porous constructs using metal powders, it will be readily appreciated that the metal powder particles may be substantially uniform or may constitute a variety of shapes and sizes, e.g., may vary in terms of their three-dimensional configuration and/or may vary in terms of their respective major dimension. Measured with respect to a given particle's major dimension, particle size may be from about 20 µm to about 100 µm, from about 25 µm to about 50 µm, or from about 50 µm to about 80 µm. The metal powder particles may be spheroids, roughly cylindrical, platonic solids, polyhedrons, plate- or tile-shaped, irregularly shaped, or any combination thereof. In preferred embodiments, the metal powder comprises particles that are substantially similarly shaped and substantially similarly sized.

In another example, the porous construct may comprise a metallic foam, such as a trabecular metal scaffold, also described above. Typically, porous constructs comprising a metallic foam are constructed by applying titanium or titanium alloy, tantalum, or niobium to a carbon foam scaffold by chemical vapor deposition. See U.S. Pat. No. 5,282,861. Those skilled in the art will readily appreciate other materials and conditions that may be used to prepare a metallic foam, of which any variation may be used in accordance with the present methods and implants.

The material comprising aspherical metallic particles may comprise the same material of which the porous construct is made, may comprise a mixture of such material and one or more different materials, or may consist of one or more materials that are each different from the material of which the porous construct is made. The material comprising aspherical metallic particles may comprise any biocompatible metal, nonlimiting examples of which include titanium, a titanium alloy (e.g., Ti-6Al-4V), a cobalt-chromium alloy, aluminum, molybdenum, tantalum, magnesium, niobium, zirconium, stainless steel, nickel, tungsten, or any combination thereof.

As used herein, "aspherical" refers to the condition whereby no more than a small proportion, e.g., no more than about 20%, preferably no more than about 10%, no more than about 5%, or no more than about 1% of the particles being applied to the porous construct are sphere-shaped. In some embodiments, no more than a small proportion of the metallic particles are spheroids (e.g., not ovoid). A given complement of particles that is applied to the porous construct may consist of a mixture of differently-shaped particles, such as a mixture of one or more roughly cylindrical, platonic solid, polyhedron, plate- or tile-shaped, and irregularly shaped particles. Preferably, the particles are irregular, meaning that the shape of most of the particles do not adopt a regular geometric conformation. The aspherical metallic particles may have an average major dimension of about 5 µm to about 1000 µm, about 10 µm to about 800 µm, about 25 µm to about 750 µm, about 50 µm to about 500 µm, or about 100 µm to about 300 µm. The particles may be substantially similarly sized, or, more preferably, the particles are a variety of different sizes, wherein each particle features a major dimension within any of the ranges provided above.

In the as-applied state, the coating may have an average thickness of about 0.01 mm to about 5.0 mm. The coating has an average thickness of about 0.05 to about 3.0 mm, about 0.1 mm to about 2.0 mm, or about 0.1 mm to about 1.0 mm. The "average thickness" represents a calculation of the thickness of the coating over the entire surface to which the coating is applied.

Shrink commonly occurs with the first sintering of a porous metallic structure. If the coated porous construct is sintered, the porous construct, the coating, or both, may undergo some shrink. For example, the average thickness of the coating may shrink by about 5% to about 15%, typically by about 10%. The characteristics of the shrink experienced by a coating can depend on whether the coating is applied to a porous metallic structure in its green state, or to a porous metallic structure that has been subjected to sintering. For example, the degree of shrink of the coating may depend on whether the porous metallic structure onto which the coating is applied has already undergone sintering. Those skilled in the art will readily appreciate that sintering may lead to shrink and that the dimensions described herein with respect to the coating should be modified appropriately when considering a coating and porous construct that may have undergone shrink.

The coating may be applied to at least one surface (portion) of the porous construct. For example, if the porous construct is spherical, the coating may be applied to one or more portions of the surface of the spherical construct. In another example, if the porous construct is a three-dimensional polyhedron, the coating may be applied to one or more facets of the polyhedron, or to at least one portion of one or more facets of the polyhedron. Thus, the coating may be applied to a single, contiguous area of the porous construct, or may be applied to one or more separate, noncontiguous segments of the surface of the porous construct. The coating may be applied in any geometrical arrangement, for example, as one or more separate geometrically-shaped patches, irregular patches, strips, spirals, lines, and the like. If the coating is applied to two or more separate segments the "average thickness" may represent a measurement of the thickness of one of such separate segments, or may represent an averaged measurement of the thickness of the coating with respect to more than one or all of the separate segments.

The material that is applied to the porous construct may comprise a mixture of metallic particles plus and an adhesive, an extractable agent, or both. Where present, the extractable agent preferably comprises a particulate material. The extractable agent may comprise one or more materials that may be dissolved in an aqueous solvent, an organic solvent, or both. Alternatively or additionally, the extractable agent may be removable by heating.

The extractable agent may comprise a salt, a sugar, a solid hydrocarbon, a urea derivative, a polymer, or any combination thereof. Nonlimiting examples include ammonium bicarbonate, urea, biuret, melamine, ammonium carbonate, naphthalene, sodium bicarbonate, sodium chloride, ammonium chloride, calcium chloride, magnesium chloride, aluminum chloride, potassium chloride, nickel chloride, zinc chloride, ammonium bicarbonate, sodium hydrogen phosphate, sodium dihydrogen phosphate, potassium dihydrogen phosphate, potassium hydrogen phosphate, potassium hydrogen phosphite, potassium phosphate, magnesium sulfate, potassium sulfate, alkaline earth metal halides, crystalline carbohydrates (including sucrose and lactose or other materials classified as monosaccharides, disaccharides, or trisaccharides), polyvinyl alcohol, polyethylene oxide, a polypropylene wax (such those available from Micro Powders, Inc., Tarrytown, N.Y., under the PROPYLTEX® trademark), sodium carboxymethyl cellulose (SCMC), or any combination thereof.

When the extractable agent comprises particles, such particles may be substantially uniform with respect to one another or may constitute a variety of shapes and sizes, e.g., may vary in terms of their three-dimensional configuration and/or may vary in terms of their respective major dimension. The extractable agent can be present in a wide variety of particle sizes and particle size distributions suitable to produce a desired pore size and pore size distribution with respect to the coating in its final state. Certain preferred particle size ranges are from about 5 μm to about 1000 μm, about 10 μm to about 800 μm, about 25 μm to about 750 μm, about 50 μm to about 500 μm, or about 100 μm to about 300 μm with respect to the major dimension of the particle. The extractable agent particles may be spheroids, roughly cylindrical, platonic solids, polyhedrons, plate- or tile-shaped, irregularly shaped, or any combination thereof. In some embodiments, the extractable agent comprises particles that are substantially differently shaped, substantially differently sized, or both. Because the size and shape of the pores of the coating that may ultimately result from processing of the coated porous construct roughly correspond to the size and shape of the particles of the extractable agent, one skilled in the art will readily appreciate that the characteristics of the particles of the extractable agent may be selected according to the desired configuration of the pores of the resulting coating.

The adhesive is preferably capable of at least temporarily binding the metallic particles to each other, and, where an extractable agent is present, at least temporarily binding the metallic particles to the extractable agent, and at least temporarily binding particles of the extractable agent to each other. The adhesive may comprise one or more materials that may be dissolved in an aqueous solvent, an organic solvent, or both. Alternatively or additionally the adhesive may be removable by heating. There are virtually no limits as to which adhesive may be used in accordance with the present invention; the adhesive (which may be a single species of adhesive or may be a mixture of two or more different adhesives) need only temporarily bond the metallic particles to each other prior to sintering of the coating and/or function as a space holder, thereby allowing the coating to retain an "open" structure by allowing the creation of space between coating particles prior to sintering. The use of an adhesive may also permit physical handling of a coated construct prior to sintering without damaging the coating. Although the coated constructs of the present disclosure have medical uses, the adhesive itself need not be biocompatible, at least because the adhesive will volatilize during the sintering of the coated construct before a sufficiently high temperature is reached at which the metallic particles of the coating become "active" and thereby subject to chemical modification by the adhesive material. Suitable adhesives include acrylic based cements, commercially available glues, latex glues, or practically any other adhesive or mixture of adhesives that satisfies the role described above.

Any of a number of different techniques may be used to apply the material to the porous construct. Generally speaking, the material may be applied by one or more of spraying, painting, sprinkling, and pouring. Particular techniques for applying the material are described more fully, infra, and some are also described in U.S. Pat. Nos. 3,855,638 & 4,206, 516, the contents of both of which are incorporated herein in their entirety.

It is not necessary that all components of the material be applied contemporaneously or in a single step (although they may be), nor is it necessary that an entire complement of one component be applied in a single step (although it may be); for example, the adhesive may be applied first, followed by application of the aspherical metallic particles and optionally the extractable agent, optionally followed by an additional step of applying the adhesive. As used herein, the application of the material refers to application of the components of the material either together and in a single step or in one or more steps that may include applying some of a component in one step and an additional quantity of that component in a separate step. Additionally, application of a component of the material (e.g., the aspherical metallic particles, adhesive, or extractable agent) can refer to the direct application of the component to a portion of the porous construct, or the application of the component to a portion of the porous construct via another component. For example, application of the adhesive may refer to the direct application of the adhesive to a surface of the porous construct, or may refer to the application of the adhesive to a coating comprising aspherical metallic particles that had been applied to the porous construct prior to the application of the adhesive.

The adhesive may be applied to the porous construct contemporaneously with the application of the aspherical metallic particles. "Contemporaneously" means that during at least part of the time that the adhesive is applied to the porous construct, the aspherical metallic particles are also applied. Thus, where the adhesive is applied for a total duration of one second, application of the aspherical metallic particles for 2 seconds after the application of the adhesive and for 0.1 seconds during the application of the adhesive will be considered to have been contemporaneous with the application of the adhesive.

In one embodiment, the aspherical metallic particles may be suspended in aqueous solution with the adhesive in order to form a slurry. The slurry may then be held in a mold around a surface of the porous construct to be coated. Alternatively, the slurry may be of a consistency such that it is self-supporting on the surface and can be painted, poured, or otherwise applied to the surface without the assistance of a mold. In either embodiment, the porous construct with the slurry coating may be heated to remove water from the coating, followed by heating, which may comprise thermal composition and sintering (e.g., in an inert or reducing atmosphere, such as hydrogen), to burn off the adhesive and fuse the coating particles to each other and to the substrate.

As used herein, "heating" preferably refers to thermal decomposition and sintering, but may refer to sintering alone. When heating comprises both thermal decomposition and sintering, the thermal decomposition is preferably contiguous with the sintering process, i.e., occurs over a period of time until the sintering temperature is reached, which permits the thermal decomposition of the adhesive and/or extractable agent prior to the commencement of the sintering stage. When present, the adhesive, the extractable agent, or both may be removable by heating. Accordingly, the present methods may further comprise heating said coated construct for a time and under conditions effective to evaporate at least a portion of said adhesive, said extractable agent, or both, while substantially maintaining said material in its position in said coating.

When a slurry is used in accordance with the previously-described embodiment in which a mold is required, the mold may be subjected to pressure during all or part of the heating process. Those skilled in the art will appreciate that the size of the individual aspherical metallic particle, the density of the coating, and the desired strength of the final coating will influence the time and/or temperature of the sintering of the construct to affix the coating, and that generally speaking, longer sintering times will produce stronger coatings. It will also be appreciated that, generally speaking, density is related to the final porosity and shear strength of the coating. The bond strength of the material comprising aspherical metal particles to the porous construct is preferably either equivalent to the overall shear strength of the underlying porous construct, or at least 3000 psi, at least 3500 psi, at least 3800 psi, or at least 4000 psi.

In another technique for applying the material to the porous construct, the aspherical metallic particles may be poured or sprinkled directly onto the desired surface, and/or into a depression formed in a surface of the porous construct (in the absence of adhesive). Subsequently, the porous construct is subjected to heating conditions to affix the coating to the construct and bring the coating to its finished state.

Yet another technique may comprise spraying a surface of the porous construct with the adhesive, suspending the porous construct in a fluidized bed of aspherical metallic particles of the desired type to form a coating by adherence of the particles to the binder. The porous construct is then removed from the fluidized bed and the adhesive is permitted to dry. After the coating is dried, the construct is subjected to heating conditions.

In an alternative procedure, the aspherical metallic particles may be mixed with an adhesive to form a slurry that is applied by spraying onto a surface of the porous construct to form the coating that is subsequently permitted to dry. After the coating is dried, the construct is subjected to heating conditions.

In another procedure, the porous construct or a portion thereof is dipped into a slurry of aspherical metallic particles and an adhesive. Excess material is allowed to drip off of the construct, and the resulting coating may then be subjected to drying conditions, which may include exposure to the ambient atmosphere. After the coating is dried, the construct is subjected to heating conditions.

The surface of the porous construct, or a portion of the porous construct to which the material is to be applied, may be roughened prior to application of the material. Without intending to be bound by any particular theory of operation, it is believed that roughening the surface of the porous construct can enhance the ability of the material to adhere to the surface of the construct to which it is applied. Various techniques for roughening the surface of a porous construct are known among those skilled in the art, and any roughening technique may be used in accordance with the present invention.

The coating may be machined following application onto the porous construct. For example, following application of the material to the porous construct, the construct may be sintered, machined, and then optionally sintered again for a time and under conditions that depend on the strength requirements or other requirements of the final coating.

More than one type of material may be applied to the porous construct, and/or more than one means of applying the material may be used, such that more than one type of coating is formed. For example, one type of material may be applied to one or more portions of a porous construct, and a second type of material may be applied to one or more different portions of the construct. The second type of material may differ from the first type of material in any of a number of different ways, such as size, shape, or type of metal of the aspherical metallic particles; density of the material and resulting coating; amount of adhesive; type of adhesive; amount, particle size, particle shape, or type of extractable agent; proportion of aspherical metal particles versus extractable agent; and the like. In other embodiments, the material may be applied by one means with respect to one or more portions of the porous construct, and applied by a second, different means with respect to one or more other portions of the porous construct. In other aspects, a coating with a certain average thickness may be applied to one or more portions of the porous construct, and a second coating with a different average thickness may be applied to one or more other portions of the construct.

As provided above, the porous construct may comprise, among other things, a metallic foam, sintered body, or a green body (i.e., an unsintered porous body). Where the porous construct comprises a green body, following the application of the material onto at least one surface in order to form a coating on the green body, the present methods may further comprise sintering the coated green body in order to form an implant. Sintering is typically performed in a vacuum furnace and those skilled in the art will readily appreciate the appropriate conditions for sintering a green body comprising a metal powder and a coating comprising metallic particles. Sintering may be followed by additional processing steps, including machining to refine the shape characteristics of the sintered body. The present invention is also directed to sintered porous bodies that are made in accordance with the described methods. The sintered porous bodies may comprise implants, such as orthopedic implants used to replace or repair any damaged or otherwise compromised element or portion of an element of a skeletal system. The present implants are characterized by, inter alia, high surface roughness and porosity and therefore provide numerous benefits associated with these property, such as mechanical stability and homogeneous ingrowth of bone and tissue, thereby leading to improved biological fixation.

In other aspects, the present invention provides methods for processing a green body comprising a powder mixture in which a metal powder and a space filler assume respective positions comprising applying a material that comprises aspherical metallic particles to at least one surface of the green body, thereby forming a coating on the green body. The green body in accordance with such methods is substantially non-porous, but may be rendered porous by the removal of the space filler while substantially maintaining the metal powder in its respective position within the green body; the removal of the space filler is described more fully infra.

The powder mixture may comprise metal powder in an amount that is about 5 percent by volume to about 45 percent by volume, preferably about 15 percent by volume to about 40 percent by volume, the balance of the powder mixture comprising the space filler. Once the space filler is removed from the green body that is formed from the mixture of the metal powder and space filler in later stages of the present methods, the resulting porosity of the green body may be about 55% to about 95%, preferably about 60% to about 85%. The powder mixture of which the green body is made may comprise about 18 wt. % to about 67 wt. % metal powder, the balance of the powder mixture comprising the space filler.

The metal powder may comprise any biocompatible metal, nonlimiting examples of which include titanium, a titanium alloy (e.g., Ti-6Al-4V), a cobalt-chromium alloy, aluminum, molybdenum, tantalum, magnesium, niobium, zirconium, stainless steel, nickel, tungsten, or any combination thereof. In accordance with known methods for forming porous constructs using metal powders, it will be readily appreciated that the metal powder particles may be substantially uniform or may constitute a variety of shapes and sizes, e.g., may vary in terms of their three-dimensional configuration and/or may vary in terms of their respective major dimension.

Measured with respect to a given particle's major dimension, the size of the particles of which the metal powder consists may be from about 20 µm to about 100 µm, from about 25 µm to about 50 µm, and from about 50 µm to about 80 µm. The metal powder particles may be spheroids, roughly cylindrical, platonic solids, polyhedrons, plate- or tile-shaped, irregularly shaped, or any combination thereof. In preferred embodiments, the metal powder comprises particles that are substantially similarly shaped and substantially similarly sized.

The space filler may be one or more materials that are soluble in an aqueous solvent, an organic solvent, or both, and may include a salt, a sugar, a solid hydrocarbon, a urea derivative, a polymer, or any combination thereof. Nonlimiting examples include ammonium bicarbonate, urea, biuret, melamine, ammonium carbonate, naphthalene, sodium bicarbonate, sodium chloride, ammonium chloride, calcium chloride, magnesium chloride, aluminum chloride, potassium chloride, nickel chloride, zinc chloride, ammonium bicarbonate, sodium hydrogen phosphate, sodium dihydrogen phosphate, potassium dihydrogen phosphate, potassium hydrogen phosphate, potassium hydrogen phosphite, potassium phosphate, magnesium sulfate, potassium sulfate, alkaline earth metal halides, crystalline carbohydrates (including sucrose and lactose or other materials classified as monosaccharides, disaccharides, or trisaccharides), polyvinyl alcohol, polyethylene oxide, a polypropylene wax (such those available from Micro Powders, Inc., Tarrytown, N.Y., under the PROPYL-TEX® trademark), sodium carboxymethyl cellulose (SCMC), or any combination thereof. Alternatively or additionally, the space filler may be removed under heat and/or pressure conditions; for example, the space filler may volatilize, melt, or otherwise dissipate as a result of heating. Examples of such space filler include ammonium bicarbonate, urea, biuret, melamine, ammonium carbonate, naphthalene, sodium bicarbonate, and any combination thereof.

The particles constituting the space filler may be substantially uniform or may constitute a variety of shapes and sizes, e.g., may vary in terms of their three-dimensional configuration and/or may vary in terms of their respective major dimension.

The space filler can be present in a wide variety of particle sizes and particle size distributions suitable to produce a desired pore size and pore size distribution. Certain preferred particle size ranges are from about 200 µm to about 600 µm, from about 200 µm to about 300 µm, and from about 425 µm to about 600 µm. The space filler particles may be spheroids, roughly cylindrical, platonic solids, polyhedrons, plate- or tile-shaped, irregularly shaped, or any combination thereof. In preferred embodiments, the space filler comprises particles that are substantially similarly shaped and substantially similarly sized. Because the size and shape of the pores of the porous construct that is eventually produced from the mixture of the metal powder and the space filler roughly correspond to the size and shape of the particles of the space filler, one skilled in the art will readily appreciate that the characteristics of the particles of the space filler may be selected according to the desired configuration of the pores of the resulting porous product. In accordance with the present invention, when the space filler comprises particles that are substantially similarly shaped and substantially similarly sized, the porosity of a porous construct that is eventually formed using the space filler of this type will be substantially uniform.

Suitable techniques for mixing a metal powder with an space filler will be readily appreciated by those skilled in the art. See, e.g., U.S. Pat. Nos. 3,852,045, 6,849,230; U.S. Pub. Nos. 2005/0249625, 2006/0002810. Ideally, the mixing results in a substantially uniform dispersion of the particles comprising the minor component of the powder mixture among the particles comprising the major part of the powder mixture. The metal powder may comprise about 18 to about 67 weight percent of the powder mixture, the balance of the powder mixture comprising the space filler. Once the space filler is removed from the green body, the resulting porosity of the green body may be about 50% to about 95%, preferably about 60% to about 85%.

Following the mixing of the metal powder with the space filler, the powder mixture may be shaped into a shaped object. The shaping process can comprise filling a mold with the powder mixture, the mold having at least roughly the three-dimensional parameters of the desired final implant product, allowing for subsequent processing steps such as machining In other embodiments, the mold need not be designed to produce near-net shape parts or parts whose molded form resembles the desired final, sintered part; molds may produce generic shapes, such as bars, rods, plates, or blocks, that may be subsequently machined in the green state to produce a part that after sintering-induced shrinkage closely approximates the desired shape of the final product, with optional machining of the sintered part. Molds and mold assemblies for such purposes are well known among those skilled the art and may allow for the preparation of bodies that are, for example, spherical, spheroid, ovoid, hemispherical, cuboid, cylindrical, toriod, conical, concave hemispherical (i.e., cup-shaped), irregular, or that adopt any other desired three-dimensional conformation. Once formed from the powder mixture in accordance with the preceding, the resulting shaped object may be compacted to form the green body. The shaped object is compacted while contained within a mold assembly. Compacting may be uniaxial, multi-axial, or isostatic. In preferred embodiments, a cold isostatic press is used to compact the shaped object into the green body. Following the compacting procedure, the resulting green body may be removed from the mold and processed. Processing may include machining or otherwise refining the shape of the green body.

The characteristics and components of the material that is applied to at least one surface of the green body, the manner of applying the material, and the characteristics of the resulting coating or coatings may be in accordance with the preceding description in connection with the inventive methods comprising applying a material to a porous construct.

In one aspect, where the coating comprises a mixture of the metallic particles and one or both of an adhesive, and an extractable agent (i.e., whether applied to the green body contemporaneously or in separate steps, such components are present in or on the resulting coating), one or more of the space filler, the adhesive, and the extractable agent are removable by heating. For example, each of the space filler, adhesive, and extractable agent may be removable by heating. Following the application of the material to at least one surface of the green body, the present methods may further comprise heating the coated green body for a time and under conditions effective to evaporate at least a portion of at least one of the space filler, the adhesive, and the extractable agent, and yet substantially maintain the metal powder in its position in the green body while substantially maintaining the metallic particles their position in the coating.

Depending on various factors such as the respective identities of one or more of the space filler, adhesive, and extractable agent, the temperature of the heating environment, and the time of heating, the removal of one or more of the space filler, adhesive, and extractable agent from the green body can range from partial to complete, and the heating of the green body preferably removes one or more of the space filler, adhesive, and extractable agent from at least the surface of the green body, down to at least about 5% of the total depth of the green body. Preferably, the thermal removal of one or more of the space filler, adhesive, and extractable agent is performed at temperatures lower than sintering temperature, in order to avoid contamination of the green body material with C, N, O, or H from organic space filler, adhesive, or extractable agent. For example, the thermal removal of one or more of the space filler, adhesive, and extractable agent may occur at less than about 100° C., which is sufficient to cause the decomposition of some space fillers, adhesives, and extractable agents, as will be readily appreciated among those skilled in the art.

In another aspect, one or more of the space filler, the adhesive, and the extractable agent are removable by exposure to one or more solvents. For example, one or more of the space filler, the adhesive, and the extractable agent may be soluble in an aqueous solvent, an organic solvent, or both. Each of the space filler, the adhesive, and the extractable agent may be removable by a single solvent, or a mixture of solvents may be used to remove one or more of the space filler, the adhesive, and the extractable agent. Preferably, a single solvent is sufficient to remove each component, where present. Thus, the instant methods may further comprise exposing the coated green body to a solvent in which one or more of the space filler, the adhesive, and the extractable agent are soluble. The exposure of the coated green body to the solvent may comprise immersing the green body in the solvent, for example, by immersing the green body in a bath comprising the solvent for a time sufficient to remove at least some of the space filler, adhesive, and extractable agent, where present. Depending on various factors such as the type of solvent chosen relative to the identity of the space filler, adhesive, and extractable agent, the temperature of the solvent, and the time of exposure to the solvent, the removal of one or more of the space filler, the adhesive, and the extractable agent from the green body can range from partial to complete. The exposure of the coated green body to the solvent in which one or more of the space filler, the adhesive, and the extractable agent are soluble preferably removes the space filler from at least the surface of the coated green body to a depth at least about 1 mm, at least about 3 mm, at least about 5 mm, at least about 7 mm, or at least about 10 mm from any given surface of the green body. The exposure of the coated green body to the solvent in which one or more of the space filler, the adhesive, and the extractable agent is soluble may remove substantially all of the space filler, adhesive, and extractable agent from the coated green body.

As indicated above, once the space filler is removed from the coated green body, the resulting porosity of the coated green body may be about 50% to about 95%, preferably about 60% to about 85%.

The present methods may further comprise sintering the coated green body. For example, following the removal of one or more of the space filler, the adhesive, and the extractable agent from the coated green body, the coated green body may be exposed to sintering conditions. In other examples, one or more of the space filler, the adhesive, and the extractable agent are removed by heating, which may comprise thermal decomposition and sintering. Sintering is typically performed in a vacuum furnace and those skilled in the art will readily appreciate the appropriate conditions for sintering a green body comprising a metal powder. Sintering may be followed by additional processing steps, including machining to refine the shape characteristics of the sintered body. The present invention is also directed to sintered porous bodies that are made in accordance with the described methods. The sintered porous bodies may comprise implants, such as orthopedic implants used to replace or repair any damaged or otherwise compromised element or portion of an element of a skeletal system. The present implants are characterized by substantially uniform porosity and therefore provide numerous benefits associated with this property, such as mechanical stability and homogeneous ingrowth of bone and tissue, thereby leading to improved biological fixation.

Figure 2:
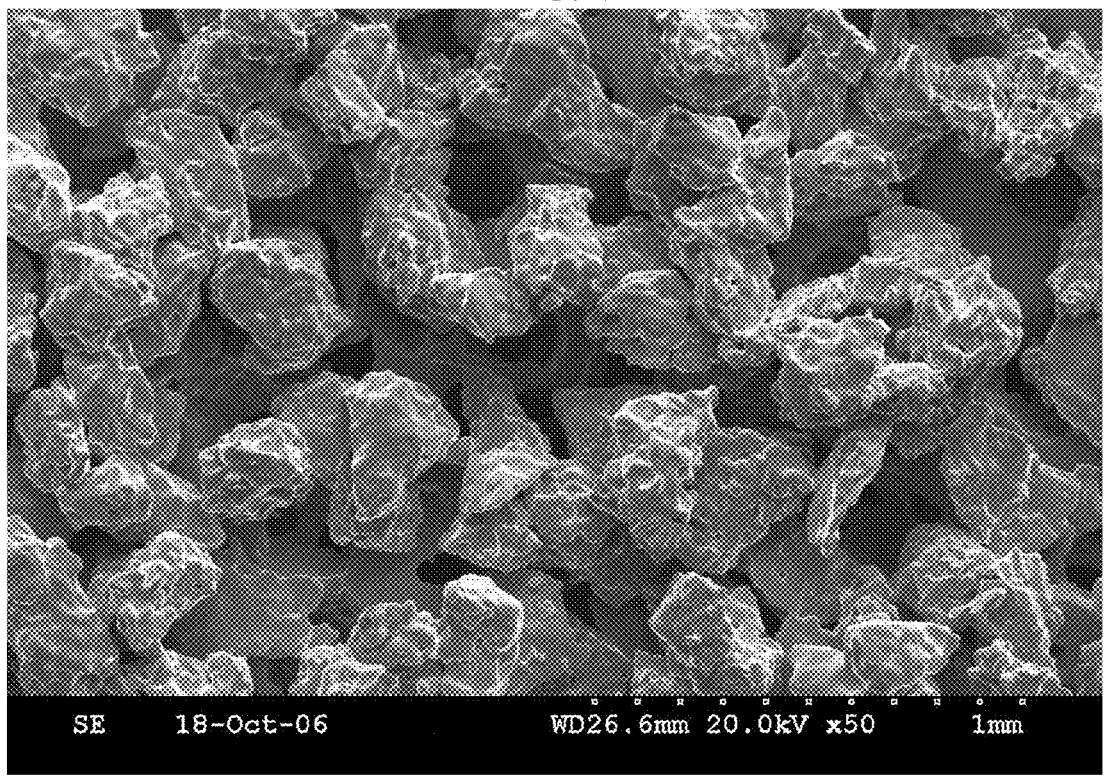
FIG. 2 is an SEM micrograph of the surface of an irregular porous coating as applied onto a porous substrate, in accordance with the present invention.

A material comprising aspherical metallic particles was applied to the surface of a porous construct. FIG. 1 shows a lateral profile (cross-section) of the irregular porous coating as applied onto the porous substrate. FIG. 2 is an SEM micrograph of the surface of the irregular porous coating as applied onto the porous substrate.

What is claimed:

1. A method for processing a green body comprising a powder mixture in which a metal powder and a space filler assume respective positions comprising applying a material that comprises aspherical metallic particles to at least one surface of said green body, thereby forming a coating on said green body.

2. The method according to claim 1 wherein said powder mixture comprises about 18 wt. % to about 67 wt. % metal powder, the balance of said powder mixture comprising said space filler.

3. The method according to claim 1 wherein said coating has an average thickness of about 0.1 mm to about 2.0 mm.

4. The method according to claim 1 wherein said material is applied by one or more of spraying, painting, sprinkling, and pouring.

5. The method according to claim 1 wherein said aspherical metallic particles have an average major dimension of about 50 µm to about 500 µm.

6. The method according to claim 1 wherein said coating comprises a mixture of said metallic particles and an adhesive, an extractable agent, or both.

7. The method according to claim 6 wherein one or more of said space filler, said adhesive, and said extractable agent are removable by heating.

8. The method according to claim 7 further comprising heating said coated green body for a time and under conditions effective to evaporate at least a portion of at least one of said space filler, said adhesive, and said extractable agent, and yet substantially maintain said metal powder in its position in said green body while substantially maintaining said metallic particles in their position in said coating.

9. The method according to claim 6 wherein one or more of said space filler, said adhesive, and said extractable agent are removable by exposure to one or more solvents.

10. The method according to claim 9 further comprising exposing said coated green body to a solvent in which one or more of the space filler, the adhesive, and the extractable agent are soluble.

11. The method according to claim 1 further comprising applying an adhesive to said porous construct contemporaneously with the application of said material.

12. The method according to claim 1 further comprising applying an adhesive onto said coating.

13. The method according to claim 1 further comprising exposing said green body to a solvent in which said space filler is soluble.

14. The method according to claim 13 wherein said space filler is soluble in an aqueous solvent, an organic solvent, or both.

15. The method according to claim 13 wherein said material further comprises an adhesive and, optionally, an extractable agent that are soluble in said solvent.

16. The method according to claim 1 further comprising sintering said coated green body, thereby forming an implant.

17. An implant made in accordance with the method of claim 16.

* * * * *